United States Patent [19]

Alter et al.

[11] Patent Number: 5,531,705
[45] Date of Patent: Jul. 2, 1996

[54] SYRINGE UNIT

[75] Inventors: Konrad G. Alter, Maylands; Newton J. Herbert, Peppermint Grove, both of Australia

[73] Assignee: Nujenko Pty Ltd, Australia

[21] Appl. No.: 66,108

[22] PCT Filed: Nov. 29, 1991

[86] PCT No.: PCT/AU91/00558

§ 371 Date: Jun. 21, 1993

§ 102(e) Date: Jun. 21, 1993

[87] PCT Pub. No.: WO92/09320

PCT Pub. Date: Jun. 11, 1992

[30] Foreign Application Priority Data

Nov. 30, 1990 [DK] Denmark ................................ 2859/90

[51] Int. Cl.$^6$ ........................................................ A61M 5/32
[52] U.S. Cl. .......................... 604/195; 604/110; 604/240
[58] Field of Search .......................... 604/110, 192–198, 604/187, 224, 228, 233, 240, 218

[56] References Cited

U.S. PATENT DOCUMENTS

| | | | |
|---|---|---|---|
| 4,233,975 | 11/1980 | Yerman | 604/110 |
| 4,747,830 | 5/1988 | Gloyer et al. . | |
| 4,932,939 | 6/1990 | Magre et al. . | |
| 4,935,015 | 6/1990 | Hall . | |
| 4,936,315 | 6/1990 | Lineback | 128/765 |
| 4,955,869 | 9/1990 | Bin | 604/195 |
| 4,955,870 | 9/1990 | Ridderheim et al. | 604/195 |
| 5,019,043 | 5/1991 | Segui Pastor et al. | 604/110 |
| 5,112,316 | 5/1992 | Venturini | 604/195 |

FOREIGN PATENT DOCUMENTS

| | | |
|---|---|---|
| 0327061 | 9/1989 | European Pat. Off. . |
| 8504590 | 10/1985 | WIPO ................................ 604/218 |
| 8912475 | 12/1989 | WIPO . |
| WO8912475 | 12/1989 | WIPO . |
| WO9100750 | 1/1991 | WIPO . |

*Primary Examiner*—C. Fred Rosenbaum
*Assistant Examiner*—J. Alexander
*Attorney, Agent, or Firm*—Harness, Dickey & Pierce

[57] ABSTRACT

A syringe unit arranged for a single-use only. The syringe unit comprises a barrel substantially closed at one end by a nozzle and open at the other end. A plunger having a piston is received in the barrel and is movable therealong. A fluid chamber is defined within the barrel between the piston and the nozzle. A syringe needle is releasably secured to the barrel with the cannula extending outwardly from the barrel and communicating with the fluid chamber and is releasable upon rotation relative to the barrel. An engaging means is provided for releasably engaging the piston with the needle whereby when so engaged the piston can be rotated to effect release of the needle from the barrel and then retracted to move the needle into a protective position within the barrel. The engaging means comprises a socket defined in a cavity provided in the needle, and a projection provided on the piston for reception in the socket and engagement therewith. The cavity provides for fluid communication between the barrel and the cannula of the needle and at least one fluid flow passage is defined between the cavity and the projection when the projection is engaged in the cavity. The fluid flow passage contributes to provision of fluid communication between the fluid chamber and the bore of the cannula.

16 Claims, 11 Drawing Sheets

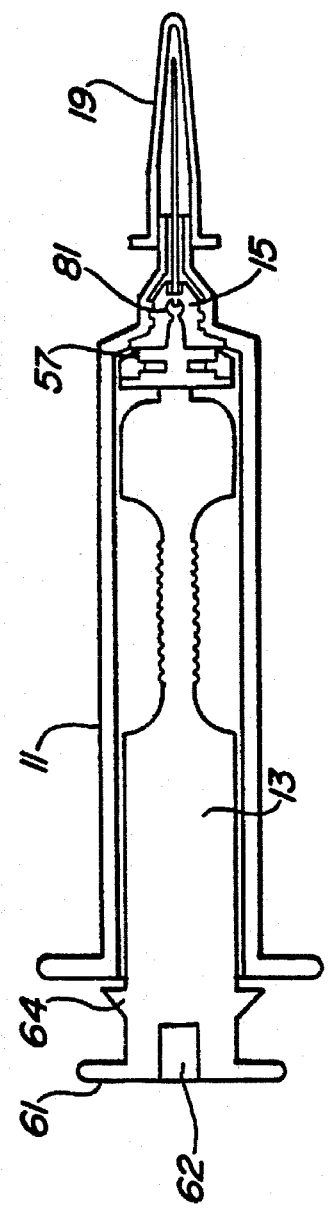
_Fig-8_
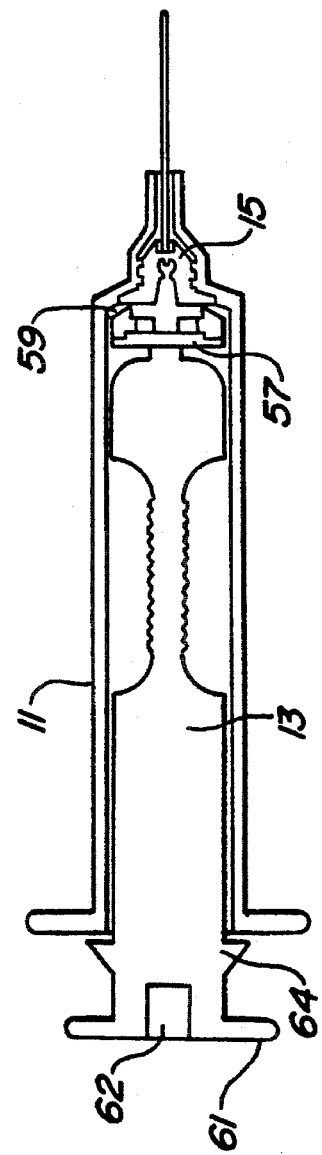
_Fig-9_
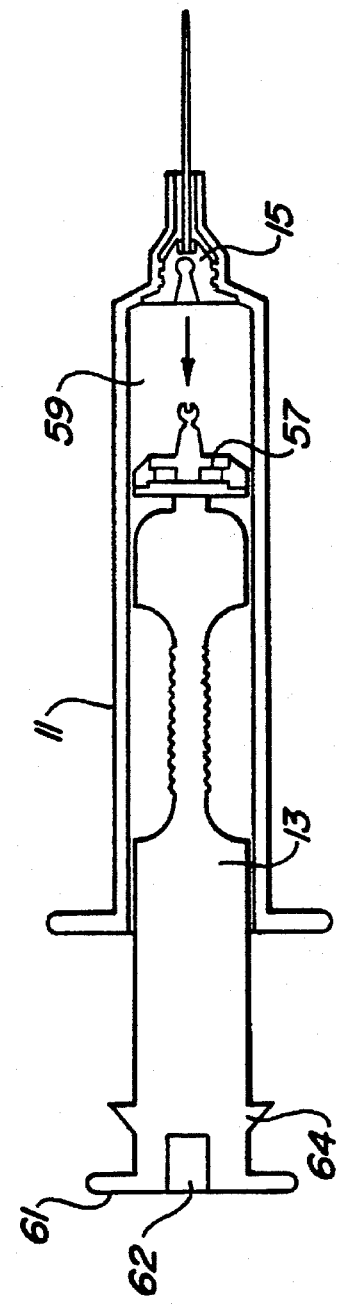
_Fig-10_

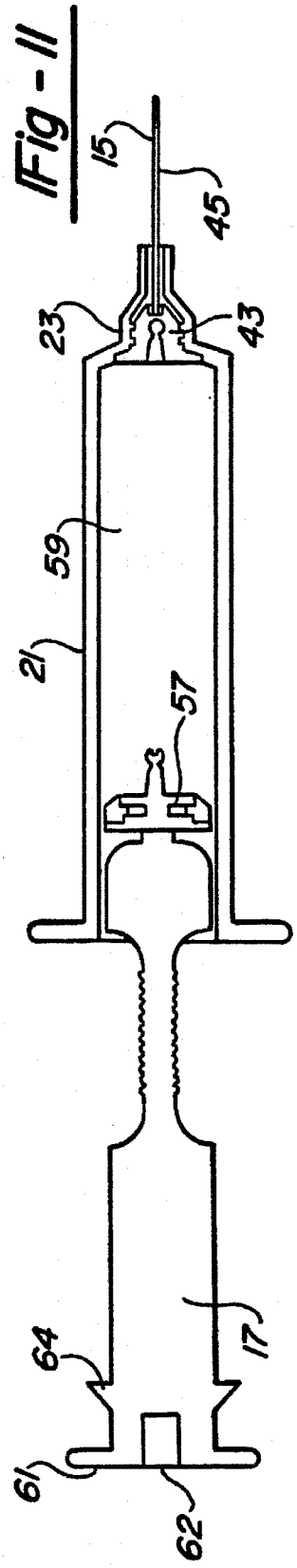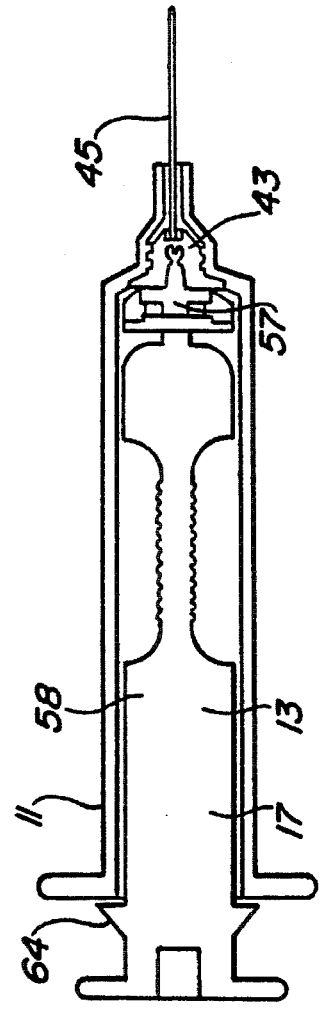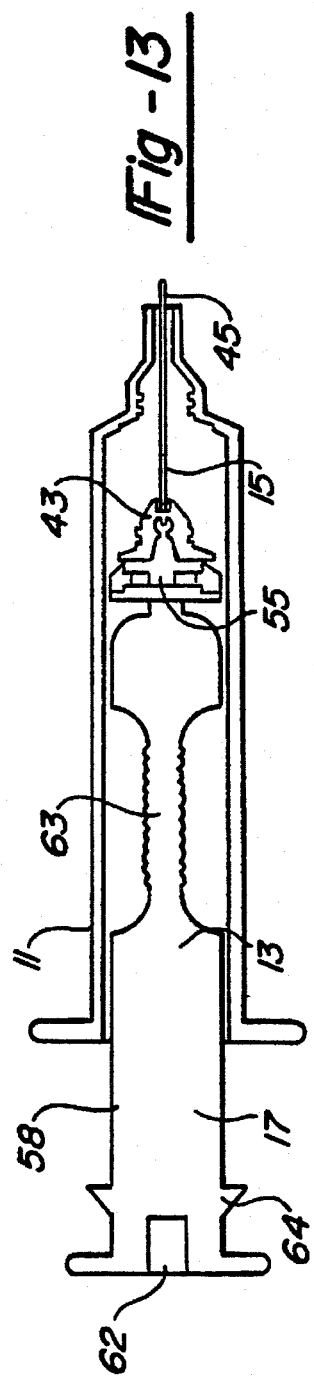

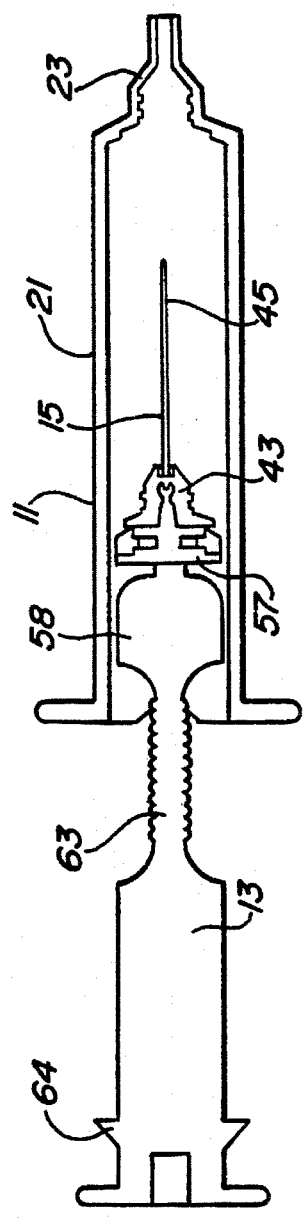
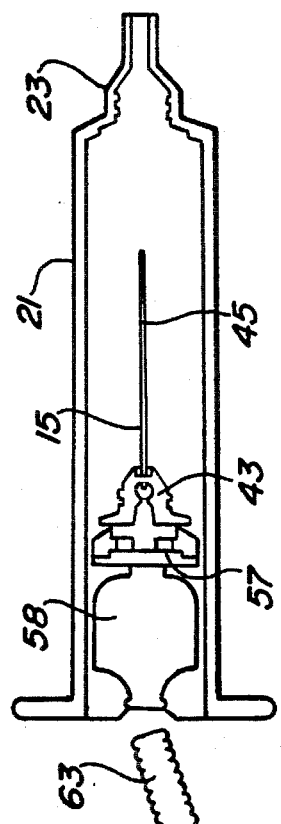
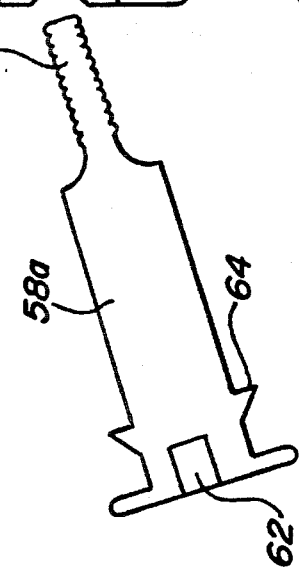
Fig-14
Fig-15
Fig-16

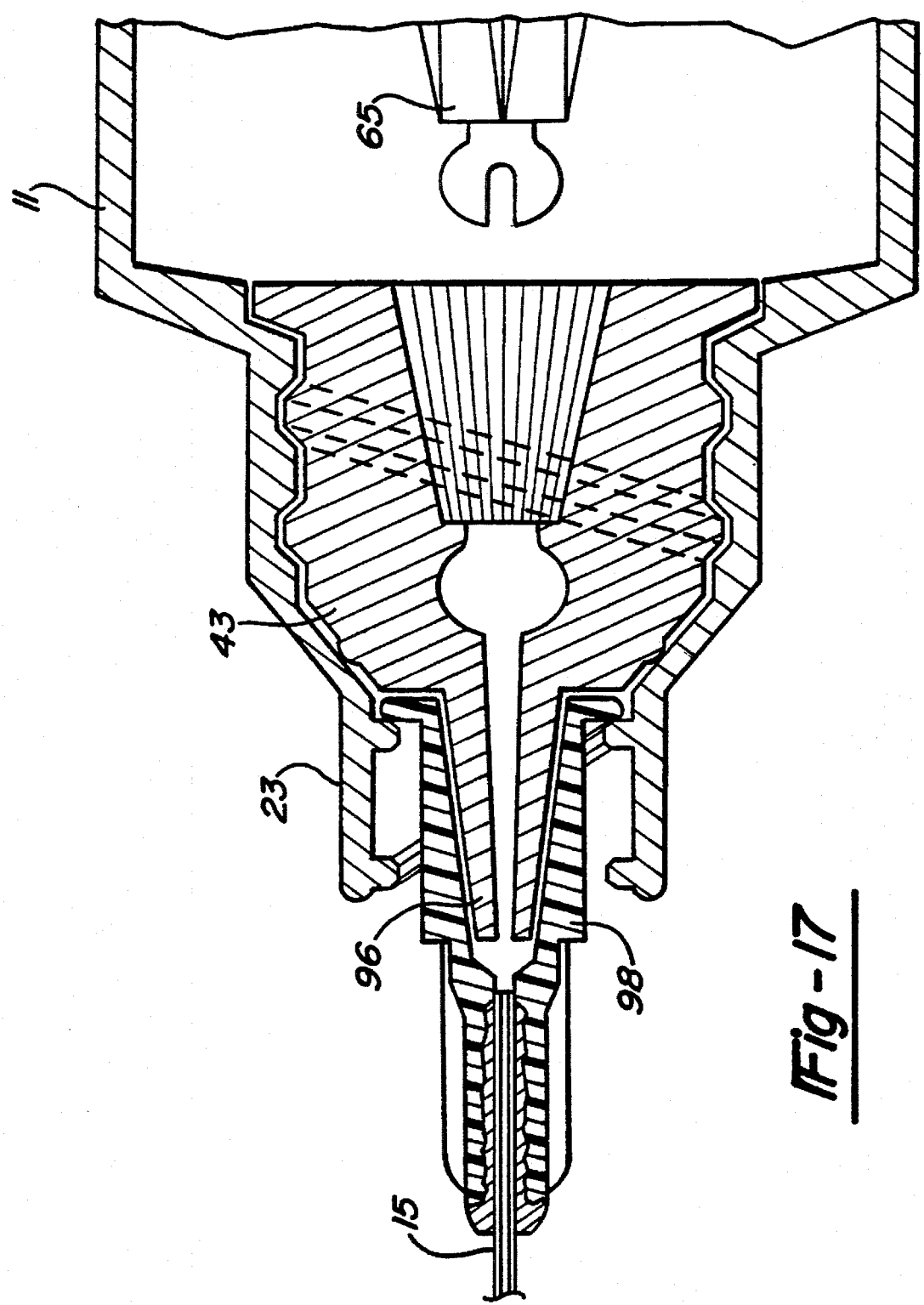

SYRINGE UNIT

TECHNICAL FIELD

THIS INVENTION relates to syringes and more particularly to a syringe unit having a needle which is retractable into a protective position after use.

BACKGROUND ART

It is well known that infectious diseases such as Hepatitis and AIDS can be transmitted through syringe needles which have become contaminated during use. Such diseases can be transmitted to health-care workers who are accidentally punctured by used syringe needles. In an endeavour the problem of accidental needle strikes, there have been various proposals for withdrawing the syringe needle into a protective position within the confines of the syringe after use of the syringe. In this way, the syringe needle is no longer exposed and the syringe can be disposed of safely. Such a syringe typically comprises a syringe barrel and a piston in reciprocal sealing engagement with the interior of the barrel. The syringe includes a retractable needle portion which normally extends from one end of the barrel. Means are provided selectively engaging the piston with the needle portion such that the needle portion can move in unison with the piston into a position in which it is wholly contained within the barrel of the syringe. Examples of such proposals are given in U.S. Pat. Nos. 4,026,287, 4,507,117 and 4,747,830.

With such syringes, the means by which the piston selectively engages the needle portion may take various forms. In many cases, however, the engaging means have not proved altogether satisfactory in that they do not perform properly or are not cost-effective in manufacture. A simple solution would appear to be an engaging means comprising a socket provided in the needle portion for receiving a spigot on the piston to provide operative engagement between the needle portion and the piston. The difficulty with this proposed solution is that injection fluid would be trapped between the socket and spigot as they move into mating relationship and so prevent effective engagement between them.

DISCLOSURE OF INVENTION

The present invention seeks to overcome the above-mentioned difficulty and to provide a novel and useful syringe unit in which the needle is retractable into a protective position.

In one form the invention resides in a syringe unit comprising a barrel substantially closed at one end by an end wall and open at the other end, a piston receivable in the barrel and movable therealong, a fluid chamber defined within the barrel between said piston and said end wall, a base for supporting a cannula, securing means for releasably securing the base of the needle portion to the barrel with the cannula extending outwardly from the barrel and the bore of the cannula communicating with said fluid chamber, said securing means being arranged to effect release of said base from the barrel upon rotation of the base relative to the barrel, and engaging means for releasably engaging the piston with said base whereby when so engaged with the base the piston can be rotated to effect release of the base from the barrel and then retracted to move the cannula into a protective position within the barrel, said engaging means comprises a cavity provided on the base and a projection provided on the piston for reception in the cavity and engagement therewith, said cavity providing for fluid communication between the barrel and the cannula, and means defining a fluid flow passage between the cavity and the projection when the projection is fully engaged in the cavity, said fluid flow passage contributing to provision of fluid communication between the fluid chamber and the bore of the cannula.

A syringe unit according to the invention may comprise a complete syringe or a cartridge-needle unit which is adapted for connection to an injection unit. Additionally, the base may comprise portion of a syringe needle or may be adapted to support a syringe needle.

Preferably, said fluid flow passage is defined by at least one channel in the projection.

Preferably, said projection is in the form of a spigot which tapers inwardly towards the free end thereof.

Preferably, said cavity is in the form of a socket which tapers inwardly in the direction of fluid flow.

Preferably, the interior wall of said socket is provided with a plurality of longitudinally extending splines.

Preferably, said spigot has a plurality of engaging ribs extending along the length of the spigot. The ribs are circumferentially spaced and preferably a respective one of said channels is defined between each pair of neighbouring ribs.

Preferably, said ribs each have a pair of longitudinal surfaces which converge outwardly to an engaging edge, said engaging edge being adapted for engagement with any one of the splines of the socket.

Preferably, said engaging means further comprises a snap fastener for providing interlocking engagement between said piston and said base.

With this arrangement, said snap fastener can provide a definite indication to a user that coupling has occurred between the piston and the base of the needle portion. This is accomplished a "clicking" action which the user can feel when coupling occurs.

For preference, said snap fastener comprises a male portion and a complementary female portion, said male portion being provided with a passage to facilitate flow of fluid from said fluid chamber to the bore of said cannula upon entry of said male portion into said female portion.

For preference, said passage comprises a further channel extending transversely across said male portion at the outer end thereof.

Preferably, said channel is adapted to allow said male portion to deform inwardly to facilitate entry into said complementary female portion.

Preferably, said male portion is provided at the free end of said projection and the female portion is formed at the innermost end of said cavity.

Preferably, said male portion comprises a neck portion and a ball portion mounted on the neck portion, said ball portion having an inner face extending between said neck portion and the outer periphery of said ball portion to define a sharp edge at said outer periphery. The sharp edge on the ball portion enhances engagement in the female portion.

In another form the invention resides in a syringe unit comprising a barrel having a nozzle at one end and being open at the other end, a piston receivable in the barrel and movable therealong, a fluid chamber defined within the barrel between said piston and said nozzle, a base for supporting a cannula, securing means for releasably securing the base to the barrel with the cannula extending outwardly from the barrel through the nozzle and the bore of the cannula communicating with said fluid chamber, said securing means being arranged to effect release of said base from the barrel upon rotation of the base relative to the barrel, and engaging means for releasably engaging the piston with said base whereby when so engaged with the base the piston can be rotated to effect release of the base from the barrel and then retracted to move the cannula into a protective position within the barrel, said engaging means including a snap fastener having a male portion and a complementary female portion, said male portion being provided with a passage to facilitate flow of fluid from the fluid chamber to the bore of the cannula upon entry of the male portion into said female portion.

For preference, said male portion is provided on said piston and said female portion is formed in said base.

BRIEF DESCRIPTION OF THE DRAWINGS

The invention will be better understood by reference to the following description of two specific embodiments as shown in the accompanying drawings in which:

FIG. 8 is a schematic view showing the syringe prior to use;

FIG. 9 is a schematic view showing the syringe with a protective cover removed;

FIG. 10 is a schematic view showing the syringe in the condition where the piston is being retracted to draw injection fluid into the syringe;

FIG. 11 is a schematic view of the syringe in readiness for an injection procedure;

FIG. 12 is a schematic view illustrating the syringe at the completion of an injection procedure with the piston in engagement with the syringe needle portion prior to retraction of the needle into a protective position within the syringe barrel;

FIG. 13 is a schematic view of the syringe during retraction of the needle portion into a protective position within the barrel;

FIG. 14 is a schematic view of the syringe at the completion of retraction of the needle portion;

FIG. 15 is a schematic view of the syringe with the needle portion in the protective position and the piston shank fractured to inhibit reuse of the syringe;

FIG. 16 is a schematic view of the syringe with the fracture portion of the shank fitted onto the syringe as a closure cap; and FIG. 17 is a fragmentary sectional view of a syringe according to the second embodiment.

MODE OF CARRYING OUT INVENTION

Figure 1:
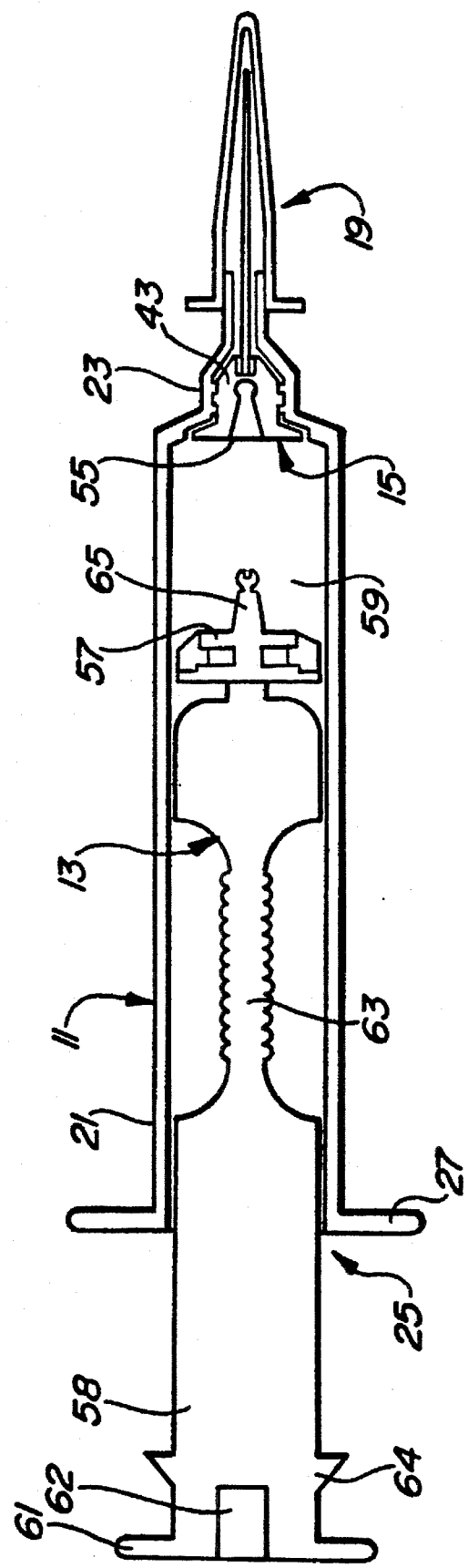
FIG. 1 is a sectional view of a hypodermic syringe according to the first embodiment.
Figure 2:
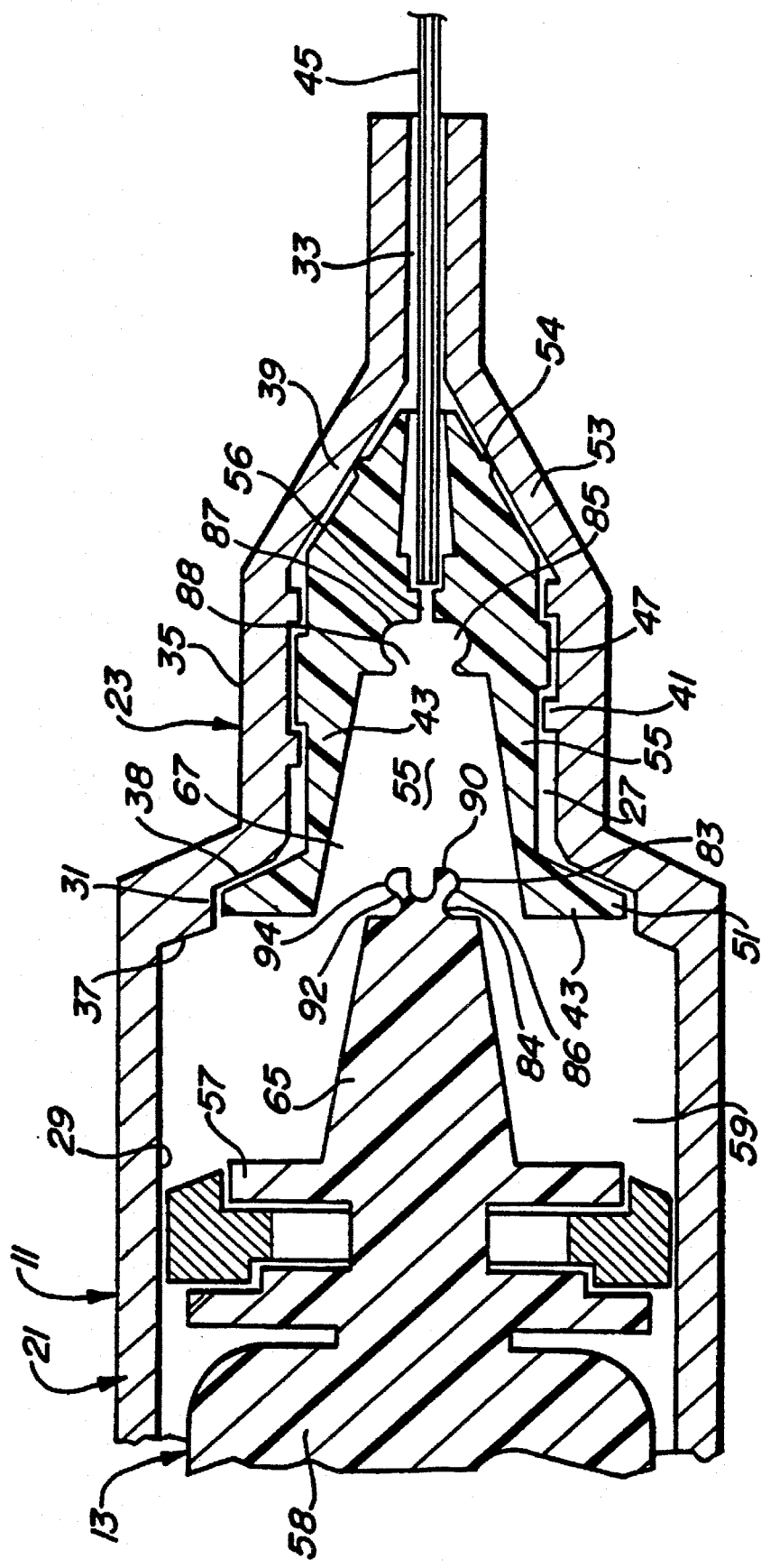
FIG. 2 is a fragmentary view of the syringe of the first embodiment showing engaging means for engaging the syringe piston with the syringe needle portion to facilitate withdrawal of the needle portion into a protective position, the arrangement being illustrated prior to such engagement.

The embodiment shown in the drawings is directed to a hypodermic syringe intended for disposal after a single use.

The syringe comprises a syringe barrel 11, a plunger 13, a needle portion 15 functioning as a syringe needle, and a protective cover 19.

The barrel 11 is formed of transparent material for viewing its contents. The barrel 11 has a cylindrical side wall 21 and a nozzle 23 at the distal end of the barrel. The nozzle 23 is formed integrally with the side wall 21 and serves to substantially close the distal end of the barrel.

The proximal end of the barrel has an opening 25. A flange 26 is formed around the opening 25 and the proximal end of the barrel to provide a means by which a user can grip the barrel while using the syringe.

The nozzle 23 defines an axial passage 27 one end of which communicates with the interior of the barrel while the other end opens onto the exterior of the barrel. The axial passage 27 comprises a series of sections including an inner axial section 31, an outer axial section 33 which is of the smallest of the section in diameter, and an intermediate axial section 35. The inner axial section 31 is joined to the inner face 29 of the cylindrical side wall 21 by a first tapered section 37. A second tapered section 38 joins the inner and intermediate axial sections 31 and 35 respectively. Similarly, a third tapered section 39 joins the intermediate and outer axial sections 35 and 33 respectively.

An internal thread formation 41 is provided on the intermediate axial section 35 of the passage 27 for releasably engaging the needle portion 15 of the syringe, as will be explained later. The internal thread formation 41 comprises a two start thread.

The needle portion 15 is detachably mountable on the barrel. The needle portion includes a base 43 formed of suitable plastics material and a cannula 45 mounted onto the base. The outer end of the cannula is formed with a sharp point 46.

The base 43 of the needle portion is adapted to be received within the axial passage 27 defined within the nozzle and has protrusions 47 for threadingly engaging the internal thread formation 41 provided on the intermediate section 35. When the base is engaged with the nozzle in this position, the cannula 45 extends through the axial section 33 of the passage and beyond the nozzle so that it is exposed for the purposes of performing an injection.

The base 43 is shaped to define various sections including a first section 51 which is radially outermost and adjacent the free end of the base, a tapered section 53 adjacent the other end of the base, and an intermediate section 55 on which said protrusions 47 are mounted. The tapered section has a sealing rib 54.

When the base is fully received within the passage 27 in the nozzle, the sealing rib 54 of the tapered section 53 of the base sealingly engages against the tapered section 39 of the passage to provide a seal therebetween and the outermost section 51 of the base engages against the inner axial section 31 of the passage to provide an axial seal therebetween.

The base 43 of the needle portion has a cavity 55 which opens onto the interior of the barrel when the base is received within the nozzle. The cavity 55 communicates with the inner end of the cannula by way of a bore passage 56. When the base is in this position, the cavity provides for fluid communication between the cannula and the interior of the barrel.

The plunger 13 comprises a piston 57 and a shank 58. The piston is received in the syringe barrel 11 and is in sliding and sealing engagement inner face 29 of the side wall of the barrel.

An injection fluid chamber 59 is defined within the barrel between the piston 57 and the nozzle 23. The volume of the fluid chamber 59 varies according to movement of the piston along the barrel.

The shank 58 is connected to the piston and extends out through the opening 25 at the proximal end of the syringe barrel. The outer end of the shank has a flange 61 to facilitate manual operation of the plunger. A socket 62 is provided in the outer end of the shank, the purpose of which will become apparent later. A stop 60 in the form of a circumferential protrusion is provided on the shank adjacent its outer end for engagement against the proximal end of the syringe barrel to limit the extent of inward movement of the shank with respect to the syringe barrel.

The shank is of generally cruciform shape in cross-section except for a weakened section 63 at a region along the length of the shank. The weakened section is of reduced width in relation to the remainder of the shank. The purpose of the weakened section is to allow the shank to be fractured upon application of a bending force to it. Fracturing of the shank effectively renders the plunger inoperable, as will be described later. This feature of the shank is disclosed in U.S. Pat. No. 4,919,652 (Alter et al).

The piston 57 and the needle portion 15 are provided with engaging means 64 which allow them to be selectively engaged for the purpose of releasing the needle portion from threaded engagement with the barrel and withdrawing it into the barrel so that the sharp end of the cannula is within the confines of the barrel. For this purpose, the piston is provided with an axial projection 65 which extends in a direction towards the distal end of the barrel. The axial projection 65 defines a spigot adapted to be snugly received in a socket 67 defined by the cavity 55 within the base 43 of the needle portion. The socket 67 opens onto the free end of the base 43 and tapers inwardly in the direction towards the cannula and is provided with a plurality of longitudinally extending splines 69 on its inner wall. The splines 69 extend for substantially the entire length of the socket. In this embodiment there are 16 of such splines.

The spigot 65 tapers inwardly towards its free end and comprises a plurality of circumferentially spaced engaging ribs 71 extending along its length. In this embodiment there are four of such ribs. The spacing between neighbouring ribs 71 defines channels 73 which permit fluid flow between the fluid chamber in the barrel and the cannula when the spigot is received in the socket, as will be explained in more detail later. The ribs each have a pair of longitudinal surfaces 77 which converge outwardly to define an engaging edge 79. The engaging edges 79 of the spigot can engage with any of the splines 69 within the socket and so there is no requirement for the socket and spigot to be in any particular orientation with respect to each other before mating can occur.

Co-operation between the spigot and the socket facilitates transmission of rotational torque from the plunger to the needle portion for the purpose of unscrewing the needle portion from the barrel to enable the needle portion to be withdrawn into the barrel.

Coupling between the piston 57 and the needle portion 15 is further accomplished by a snap fastener 81 which is adapted to transmit an inwardly directed axial force from the piston to the needle portion. The snap fastener is necessary in this embodiment for the reason that frictional engagement between the spigot and the socket may not be sufficient to accommodate the necessary axial force to withdraw the needle portion.

The snap fastener 81 completes coupling between the piston 57 and the needle portion 15 when the shank 58 is at its innermost position with respect to the syringe barrel 11, as determined by the stop 60.

The snap fastener 81 comprises a male portion 83 on the free end of the spigot and a complementary female portion 85 at the inner end of the socket 67. The male portion 83 is in the form of a stud which is formed integrally with the spigot and which comprises a neck portion 84 and a ball portion 86. The female portion 85 is in the form of a corresponding cup having a side wall 87 and an open mouth 88. The stud 83 is engagable with the cup by virtue of the inherent resilience of the materials from which those two components are formed. The bore passage 56 extends between the inner end of the cup and the cannula for fluid flow.

The ball portion 86 of the stud includes a generally spherical outer face 90 and an inner face 92 extending between the neck portion 84 and the outer face 90. The inner face 92 extends in a radial direction to define a sharp edge at the junction 94 between the outer face and the inner face. The sharp edge is adapted to engage the wall 87 of the cup 85 to enhance engagement between the stud and the cup.

Figure 3:
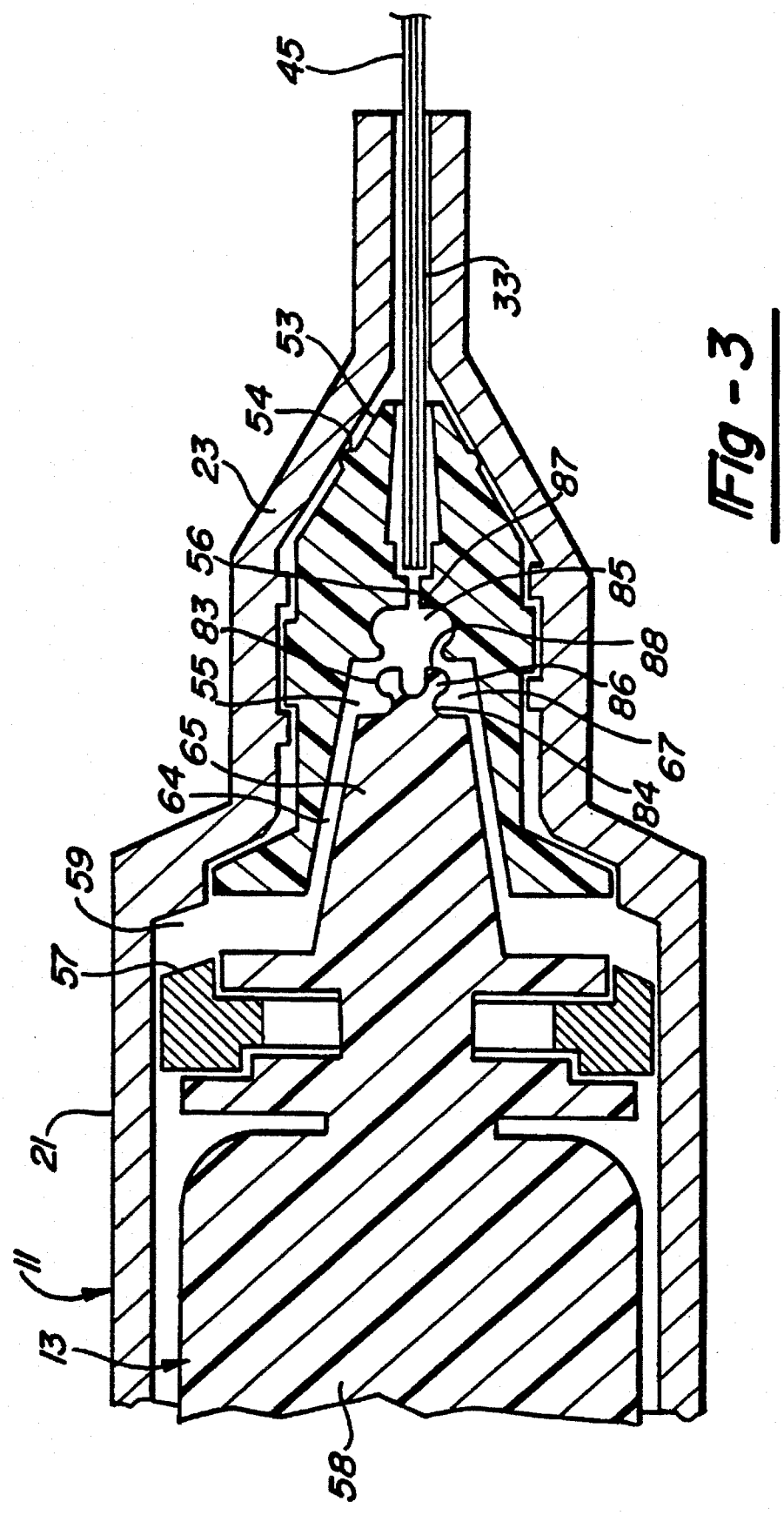
FIG. 3 is a view similar to FIG. 2 with the exception that the arrangement is illustrated at the commencement of engagement between the syringe piston and the needle portion.
Figure 4:
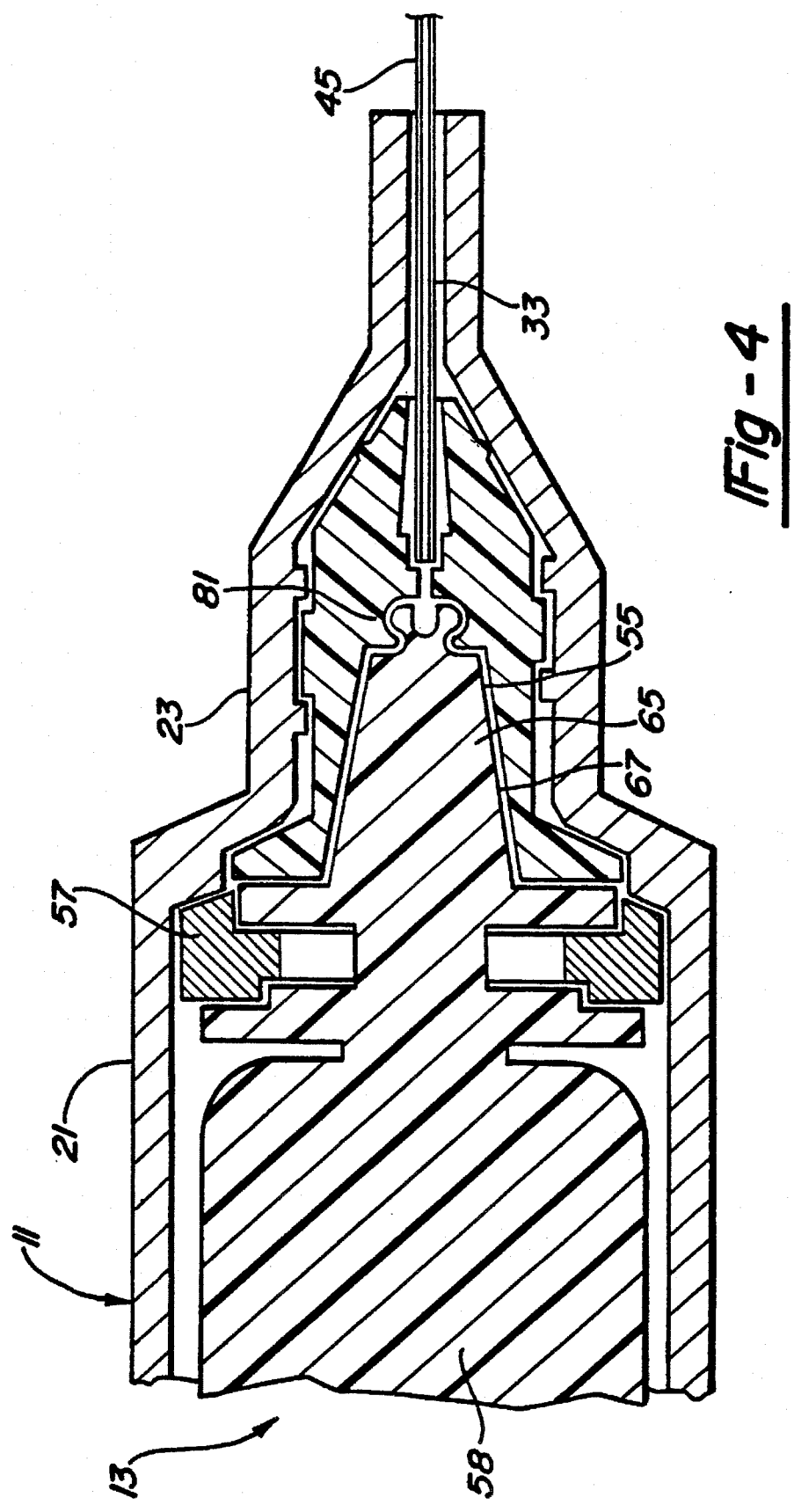
FIG. 4 is also a view similar to FIG. 2 with the exception that the arrangement is illustrated at completion of engagement between the syringe piston and the needle portion.
Figure 5:
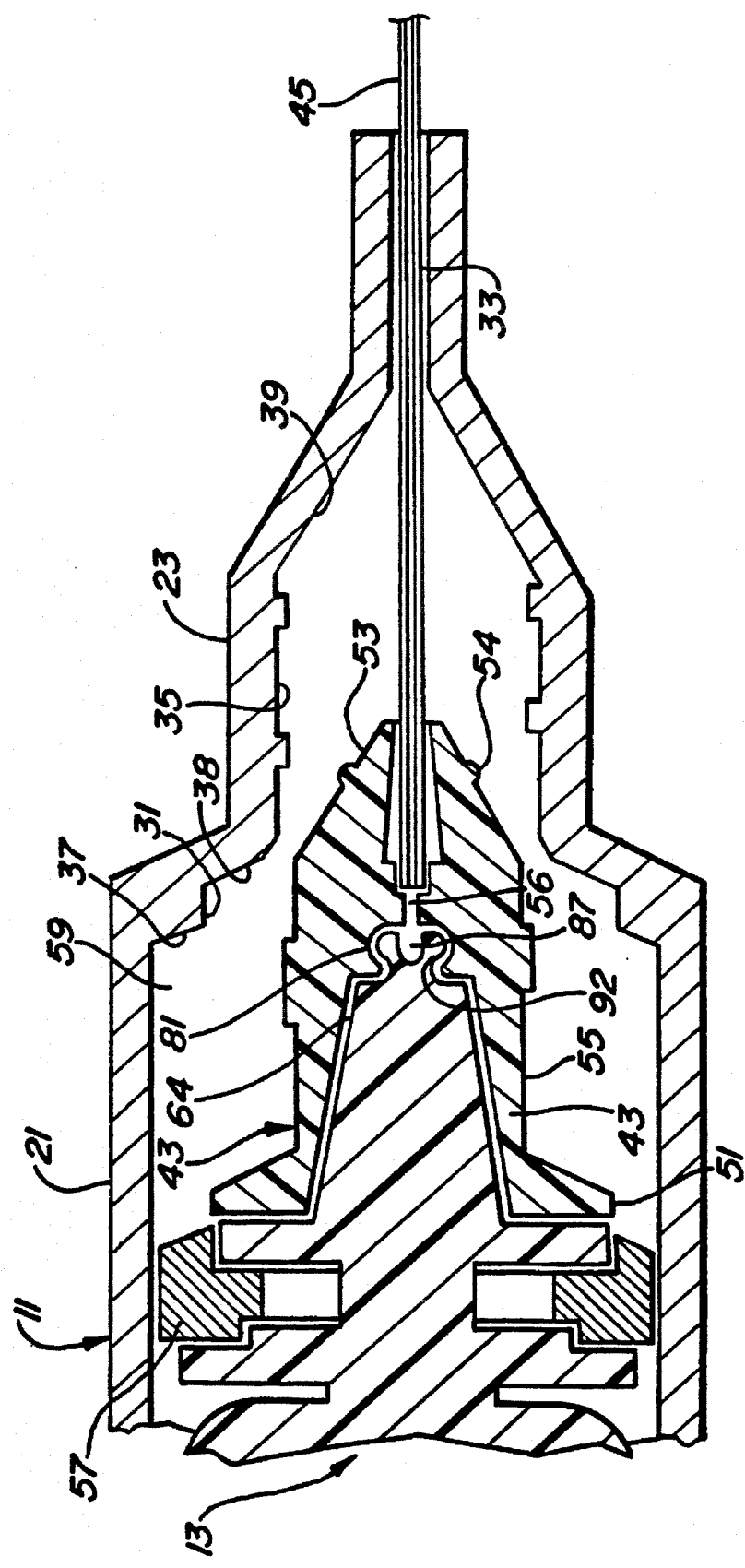
FIG. 5 is also a view similar to FIG. 2 with the exception that the arrangement is illustrated at the stage where the needle portion is being withdrawn into the protective position.
Figure 6:
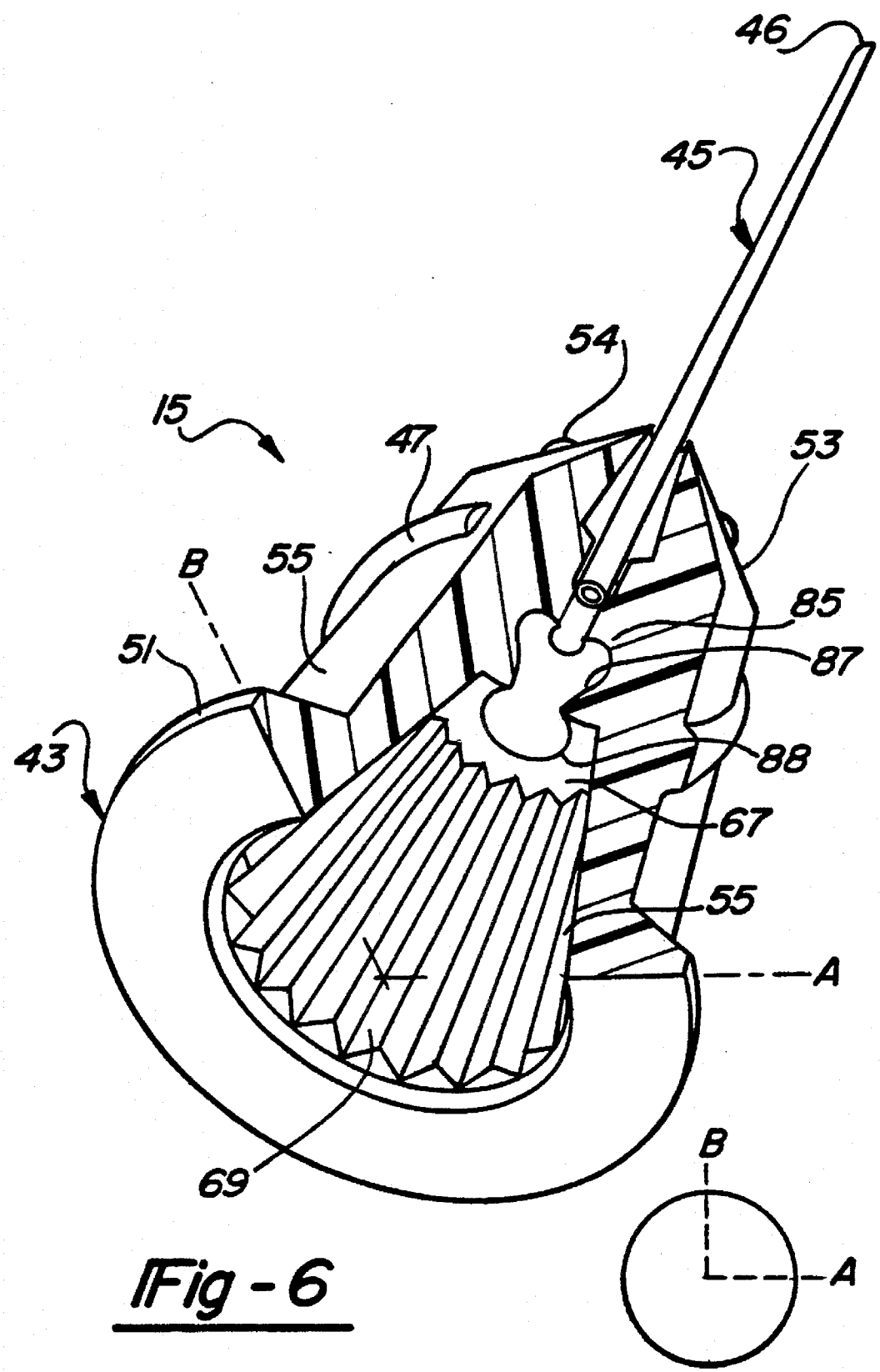
FIG. 6 is a perspective view in angle section of the needle portion showing a socket in the needle portion which socket forms part of the engaging means.
Figure 7:
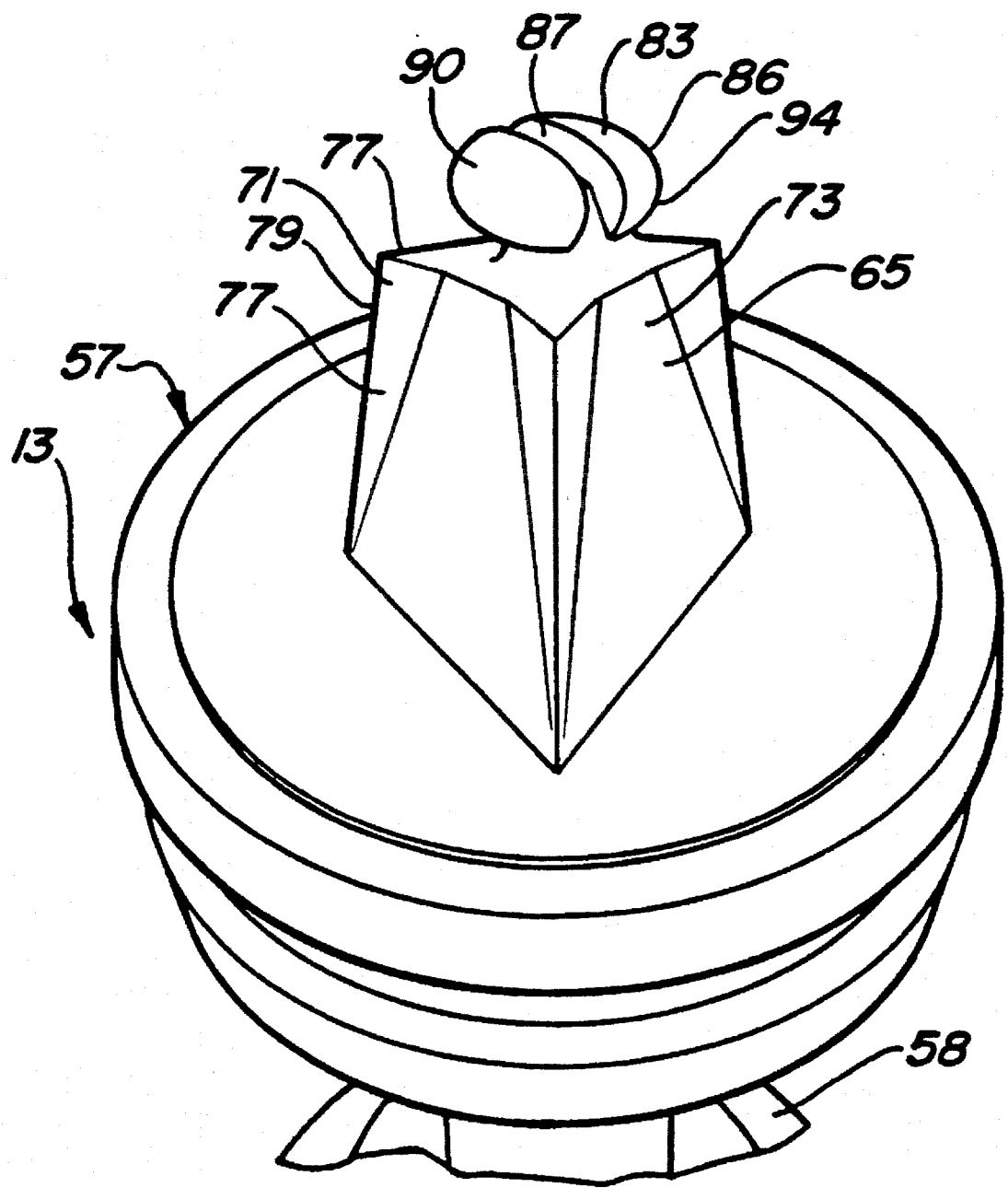
FIG. 7 is a perspective view of a spigot which forms part of the engaging means.

The ball portion 86 of the stud 83 is provided with a passage 87 along which injection fluid can flow to enter the cup 85 from the socket at the stage when the stud moves into engagement with the cup, as shown in FIG. 3 of the drawings. Without the passage 87, the stud might block fluid flow with the result that hydraulic pressure could develop between the piston 57 and the nozzle 23 to resist continued movement of the piston in the final stages of the injection procedure. In this embodiment the passage 87 comprises a channel extending transversely across the stud at the outer end thereof and effectively divides the stud into two lateral sections which can deflect inwardly to assist entry of the stud into the cup.

When the stud 83 of the snap fastener 81 enters the cup 85, the user can feel a "clicking" action which provides an indication that the piston has reached the extremity of its movement and that coupling between the piston and the needle portion has occurred. Coupling is also confirmed by the presence of the stop 60 on the shank in engagement with the outer end of the syringe barrel. This confirmation can be useful as there may be situations where the user of the syringe may fail to feel the "clicking action" generated by the snap fastener. The confirmation of coupling provided by engagement between the stop and the syringe barrel eliminates any uncertainty as to whether coupling has occurred.

With the piston coupled to the needle portion, rotational torque produced by rotating the plunger about its longitudinal axis is transmitted through the spigot and socket to the base of the needle portion. The rotational torque transmitted to the base effects rotation of the base to unscrew the needle portion from the nozzle. Once the needle portion has been unscrewed from the nozzle, withdrawal of the plunger causes the needle portion to retract into the barrel, the retracting force being transmitted from the plunger to the needle portion by frictional engagement between the spigot and the socket and the interlocking action of the snap fastener.

Operation of the syringe according to the embodiment will now be described in relation to FIGS. 8 to 16 of the accompanying drawings. The syringe is shown in a stored position with the protective cover 19 in place in FIG. 8 of the drawings. When the syringe is to be used, the protective cover is removed. Fluid for injection into the body of a patient is drawn into the syringe by retracting the plunger 13, as shown FIG. 10 of the drawings. At this stage, the syringe is in the position shown in FIG. 11 where it is in readiness for injection of the fluid previously drawn into the barrel. The cannula is inserted into the body of the patient and the plunger pushed inwardly thereby to force the injection fluid through the needle portion into the body of the patient. The path followed by the fluid from the injection chamber is through the socket, the cup and the bore passage to the inner end of the cannula. The axial seal established between the base of the needle portion and the nozzle inhibits wastage of injection fluid and reduces dead space at the completion of the injection procedure. As the piston approaches the needle portion towards the end of the injection stage, the spigot on the piston enters the socket defined within the base. As the spigot continues to advance towards the inner end of the socket, the stud of the snap fastener on the spigot enters the cup formed in the base and provides a "clicking" action on completion of the engagement to provide an indication to the user that the spigot has been fully received in the socket. The channels 73 defined between the engaging ribs 71 on the spigot serve to maintain a fluid flow path through the socket which flow path might otherwise be blocked or impeded once the spigot has entered the socket. Similarly, the transverse channel 87 in the stud 83 ensure that fluid discharging from the fluid chamber towards the cannula is not blocked by engagement between the piston and the needle portion. In this way, the injection fluid does not prevent full movement of the plunger and proper coupling between the piston and the needle portion. After the injection has been completed, the plunger is rotated in the direction appropriate to unscrew the needle portion from the nozzle, as shown in FIG. 12 of the drawings. After the needle portion has been unscrewed from the nozzle, the plunger is retracted to withdraw the needle portion into a protective position within the barrel, as shown in FIG. 11. The needle portion is shown fully received in a protective position within the barrel of the syringe in FIG. 14 of the drawings. At this stage, the shank of the plunger can be fractured at the weakened section to inhibit subsequent use of the syringe. The shank is fractured by applying a bending force to the shank. On fracturing of the shank, the portion 58a thereof outwardly of the weakened section separates from the remainder of the shank and can function as a closure cap for the nozzle 23, as shown in FIG. 16. To function as a closure cap, the shank portion 58a is fitted onto the nozzle with the outer end of the nozzle received in socket 62.

Referring now to FIG. 17 of the drawings, the syringe according to the second embodiment is similar to the first embodiment with the exception that the base 43 is not formed by part of a syringe needle but rather is separate from the syringe needle 15 and is adapted to support the syringe needle which may be of known kind. In this embodiment the base 43 has a fitting 96 in the form of a spigot which receives and supports the hub 98 of the syringe needle.

It should be appreciated that the scope of the invention is not limited to the scope of the embodiment described. In particular, it should be understood that the syringe unit according to the invention may be a complete syringe in itself or a syringe unit for use with a suitable injection unit such as that described in U.S. Pat. No. 4,642,103.

We claim:

1. A syringe unit comprising a barrel substantially closed at one end by an end wall and open at the other end, a piston receivable in the barrel and movable therealong, a fluid chamber defined within the barrel between said piston and said end wall, a base for supporting a cannula, securing means for releasably securing the base to the barrel with the cannula extending outwardly from the barrel and the bore of the cannula communicating with said fluid chamber, said securing means being arranged to effect release of said base from the barrel upon rotation of the base relative to the barrel, and engaging means for releasably engaging the piston with said base whereby when so engaged with the base the piston can be rotated to effect release of the base from the barrel and then retracted to move the cannula into a protective position within the barrel, said engaging means comprises a cavity provided on the base and a projection provided on the piston for reception in the cavity and engagement therewith such that said projection is snap fit into said cavity so as to define means defining a fluid flow passage between the cavity and the protection, said cavity providing for fluid communication between the barrel and the cannula, and said fluid flow passage contributing to provision of fluid communication between the fluid chamber and the bore of the cannula.

2. A syringe unit according to claim 1 wherein said means defining said fluid flow passage comprises at least one channel in the projection.

3. A syringe unit according to claim 2 wherein said projection comprises a spigot which tapers inwardly towards a free end thereof and wherein said cavity comprises a socket which tapers inwardly in the direction of fluid flow.

4. A syringe unit according to claim 3 wherein the interior wall of said socket is provided with a plurality of longitudinally extending splines and wherein said spigot has a plurality of engaging ribs extending along the length of the spigot for engagement with the splines.

5. A syringe unit according to claim 4 wherein said ribs are circumferentially spaced and a respective one of said channels is defined between each pair of neighbouring ribs.

6. A syringe unit according to claim 1 wherein said projection comprises a spigot which tapers inwardly towards a free end thereof and wherein said cavity comprises a socket which tapers inwardly in the direction of fluid flow.

7. A syringe unit according to claim 6 wherein the interior wall of said socket is provided with a plurality of longitudinally extending splines and wherein said spigot has a plurality of engaging ribs extending along the length of the spigot for engagement with the splines.

8. A syringe unit according to claim 1 or 2 wherein said engaging means further comprises a snap fastener for providing interlocking engagement between said piston and said base.

9. A syringe unit according to claim 8 wherein said snap fastener comprises a male portion and a complementary female portion, and wherein said means defining a fluid flow passage further comprises a passage to facilitate flow of fluid from said fluid chamber to the bore of said cannula upon entry of said male portion into said female portion.

10. A syringe unit according to claim 9 wherein said passage comprises a further channel extending transversely across said male portion at the outer end thereof.

11. A syringe unit according to claim 10 wherein said further channel is adapted to allow said male portion to deform inwardly to facilitate entry into said complementary female portion.

12. A syringe unit according to claim 9 wherein said male portion comprises a neck portion and a ball portion mounted on the neck portion, said ball portion having an inner face extending between said neck portion and the outer periphery of said ball portion to define a sharp edge at said outer periphery.

13. A syringe unit according to claim 9 wherein said male portion is provided at a free end of said projection and the female portion is formed at the innermost end of said cavity.

14. A syringe unit comprising a barrel having a nozzle at one end and being open at the other end, a piston receivable in the barrel and movable therealong, a fluid chamber defined within the barrel between said piston and said nozzle, a base for supporting a cannula, securing means for releasably securing the base to the barrel with the cannula extending outwardly from the barrel through the nozzle and the bore of the cannula communicating with said fluid chamber, said securing means being arranged to effect release of said base from the barrel upon rotation of the base relative to the barrel, and engaging means for releasably engaging the piston with said base whereby when so engaged with the base the piston can be rotated to effect release of the base from the barrel and then retracted to move the cannula into a protective position within the barrel, said engaging means including a snap fastener having a male projecting portion and a complementary female cavity portion, said male projecting portion being provided with a passage to facilitate flow of fluid from the fluid chamber to the bore of the cannula upon snap fitting the male projecting portion into said female cavity portion.

15. A syringe unit according to claim 1 or 14 wherein the base comprises a portion of a syringe needle.

16. A syringe unit according to claim 1 or 14 wherein the base is adapted to support a syringe needle.

* * * * *

UNITED STATES PATENT AND TRADEMARK OFFICE
CERTIFICATE OF CORRECTION

PATENT NO. : 5,531,705

DATED : July 2, 1996

INVENTOR(S) : Konrad G. Alter et al.

It is certified that error appears in the above-identified patent and that said Letters Patent is hereby corrected as shown below:

Column 8, line 26, Claim 1, "protection" should be -- projection --.

Signed and Sealed this

Eighth Day of October, 1996

Attest:

BRUCE LEHMAN

Attesting Officer

Commissioner of Patents and Trademarks